United States Patent [19]

Kiehs et al.

[11] 4,129,601

[45] Dec. 12, 1978

[54] PYROCATECHOL DERIVATIVES

[75] Inventors: Karl Kiehs, Lampertheim; Rolf Huber, Ludwigshafen, both of Fed. Rep. of Germany

[73] Assignee: BASF Aktiengesellschaft, Ludwigshafen am Rhein, Fed. Rep. of Germany

[21] Appl. No.: 710,415

[22] Filed: Aug. 2, 1976

Related U.S. Application Data

[63] Continuation-in-part of Ser. No. 409,309, Oct. 24, 1973, abandoned, and Ser. No. 409,330, Oct. 24, 1973, abandoned.

[30] Foreign Application Priority Data

Oct. 25, 1972 [DE] Fed. Rep. of Germany ....... 2252250

[51] Int. Cl.$^2$ .............................................. C07C 43/22
[52] U.S. Cl. .................... 568/593; 568/649; 568/652; 568/653; 260/347.8; 260/345.9 R; 560/144; 568/644
[58] Field of Search .................. 260/613 D, 613 R

[56] References Cited

U.S. PATENT DOCUMENTS

| 1,792,716 | 2/1931 | Stockelbach | 260/613 D X |
| 2,508,917 | 5/1950 | Harris et al. | 260/613 D X |
| 2,528,139 | 10/1950 | Harris et al. | 260/613 D X |

OTHER PUBLICATIONS

Mamedov et al., Chemical Abstracts, vol. 58, (1963) 466.

*Primary Examiner*—Bernard Helfin
*Attorney, Agent, or Firm*—Keil, Thompson & Shurtleff

[57] ABSTRACT

New and valuable pyrocatechol derivatives and a process for their preparation. The pyrocatechol derivatives have the formula

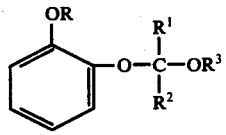

(I)

wherein:
R denotes alkyl of from 1 to 4 carbon atoms which may be substituted with halogen; alkenyl having up to 4 carbon atoms which may be substituted with halogen; alkynyl having up to 5 carbon atoms which may be substituted with halogen; or benzyl;
R$^1$ denotes hydrogen or alkyl of from 1 to 4 carbon atoms;
R$^2$ denotes benzyl or alkyl of from 1 to 3 carbon atoms which may be substituted with halogen, methoxy or ethoxy;
R$^3$ denotes alkyl of from 1 to 4 carbon atoms; cycloalkyl of from 3 to 7 carbon atoms; $\beta$-chlorethyl; methoxyethyl; ethoxyethyl; alkenyl of from 2 to 4 carbon atoms; alkynyl of from 2 to 4 carbon atoms; acetyl; propionyl;
R$^1$ and R$^2$ when taken together with the carbon atom to which they are attached form a cyclopentyl or cyclohexyl ring; and
R$^1$ and R$^3$ when taken together with the carbon atom and oxygen atom to which they are attached form a tetrahydrofuranyl or tetrahydropyranyl ring.

These compounds I are valuable starting materials for cleavage of the acetal structure to yield a pyrocatechol monoether of the formula

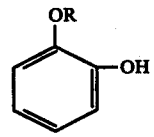

in very high yields while retaining the R member, such monoethers preferably being reacted with methyl isocyanate to form N-methylcarbamates which have a pesticidal action.

4 Claims, No Drawings

PYROCATECHOL DERIVATIVES

This application is a continuation-in-part of our earlier U.S. application Ser. No. 409,309, filed Oct. 24, 1973, and Ser. No. 409,330, filed Oct. 24, 1973, the disclosures of which are incorporated herein by reference as fully as if set forth in their entirety. Both of these earlier filed applications are now abandoned.

The present invention relates to new and valuable pyrocatechol derivaties and the process for their preparation.

It is known to prepare bis-ethers of pyrocatechol by alkylation with an alkylating agent in the presence of base. The usual methods, however, lead to symmetrical diethers. In order to produce unsymmetrical diethers, it is necessary to initially carry out a partial alkylation to produce a monoether and this entails many difficulties such as low yield.

German Pat. No. 566,033 discloses that alcoholic or phenolic hydroxyl groups are capable of reacting with vinyl or α-halo-ethers with the formation of acetals which are stable to alkali (cf. also Houben-Weyl, "Methoden der organischen Chemie", volume 6/3, pages 186 and 229).

It is also known (for example from B. J. Chem. Soc., 1927, 1664; U.S. Pat. No. 3,202,573) that in an attempt to carry out a partial alkylation of only one hydroxyl group of pyrocatechol this latter and the alkylating agent are lost in considerable quantities due to the formation, as byproduct, of the nonexploitable symmetrical diether.

We have now found that valuable new bis-ethers of pyrocatechol having the general formula I

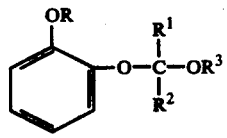

wherein:
R denotes alkyl of from 1 to 4 cabon atoms which may be substituted with halogen, alkenyl having up to 4 carbon atoms which may be substituted with halogen, alkynyl having up to 5 carbon atoms which may be substituted with halogen, or benzyl;
$R^1$ denotes hydrogen or alkyl of from 1 to 4 carbon atoms;
$R^2$ denotes benzyl or alkyl of from 1 to 3 carbon atoms which may be substituted with halogen, methoxy or ethoxy;
$R^3$ denotes alkyl of from 1 to 4 carbon atoms, cycloalkyl of from 3 to 7 carbon atoms, β-chlorethyl, methoxyethyl, ethoxyethyl, alkenyl of from 2 to 4 carbon atoms; alkynyl of from 2 to 4 carbon atoms, acetyl, propionyl;
$R^1$ and $R^2$ when taken together with the carbon atom to which they are attached form a cyclopentyl or cyclohexyl ring; and
$R^1$ and $R^3$ when taken together with the carbon atom and oxygen atom to which they are attached form a tetrahydrofuranyl or tetrahydropyranyl ring; can be obtained in a simple manner and in excellent yields.

The pyrocatechol bis-ethers of the general formula I are obtained by alkylation of novel pyrocatechol ethers of the general formula II

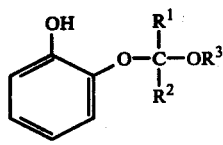

where $R^1$, $R^2$ and $R^3$ have the above meanings, by treating II with alkylating agents RX, such as alkyl sulfates, alkyl aryl sulfonates, or alkyl alkenyl and alkynyl halides having linear or branched alkyl radicals which may be substituted by halogen (Cl Br, I), or with aralkyl halides (benzyl) in an alkaline medium in accordance with the following equation:

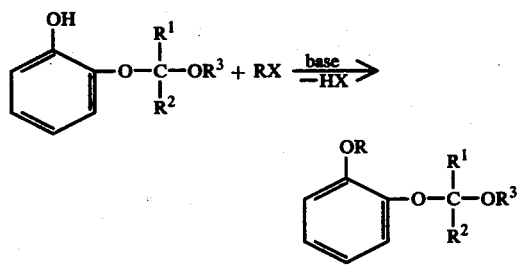

The radicals R, $R^1$, $R^2$ and $R^3$ have the above meanings.

The alkylation conditions (temperature, pressure, solvents and base) are the same as in conventional ether syntheses (cf. Houben-Weyl, Methoden der organischen Chemie, 6/3, p. 83). To carry out the following reaction, e.g.,

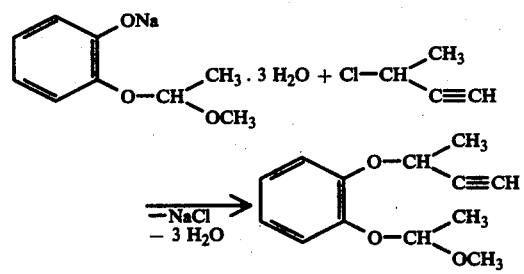

the sodium salt in its hydrated or dehydrated form, e.g., in acetonitrile or dimethyl formamide, is heated under reflux with a slight excess of 1-butyn-3-yl chloride until the solution shows a neutral reaction. Etherification proceeds with good yields.

Examples of other analogous pyrocatechol derivatives are given below:

| $R^1$ | $R^2$ | $R^3$ | $R^4$ | b.p. ° C |
|---|---|---|---|---|
| H | H | $CH_3$ | $i\text{-}C_3H_7$ | 0.1 mm: 82 to 85 |
| H | H | $CH_3$ | $-CH\genfrac{}{}{0pt}{}{CH_3}{C\equiv CH}$ | 0.1 mm: 100 to 103 |

-continued

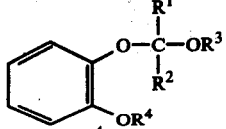

| R¹ | R² | R³ | R⁴ | b.p. °C |
|---|---|---|---|---|
| H | H | C₂H₅ | —CH(CH₃)(C≡CH) | 0.1 mm: 104 to 106 |
| H | CH₃ | CH₃ | i-C₃H₇ | 0.2 mm: 60 to 66 |
| H | CH₃ | CH₃ | —CH(CH₃)(C≡CH) | 0.2 mm: 100 to 110 |
| H | CH₃ | C₂H₅ | —CH(CH₃)(C≡CH) | 0.2 mm: 100 to 111 |
| H | CH₃ | CH₃ | —CH₂—CH=CH₂ | 0.3 mm: 100 to 103 |
| H | CH₃ | CH₃ | —CH₂—C≡CH | 0.3 mm: 85 to 91 |
| H | CH₃ | CH₃ | —CH₂—C(=CH₂)(CH₃) |  |
| H | CH₃ | CH₃ | —CH₂—CH=CH—CH₃ |  |
| H | CH₃ | CH₃ | —CH₂—C₆H₅ | 0.2 mm: 130 to 150 |

The following examples demonstrate the preparation of the ethers.

EXAMPLE 1a o-(1-methoxyethoxy)-phenol, sodium salt . 3 H₂O

In an Erlenmeyer flask 200 parts by weight of 20 percent (by weight) aqueous caustic solution is added, under nitrogen, to 168 parts by weight of o-(1-methoxyethoxy)-phenol. The mixture is briefly shaken and allowed to stand for 1 hour at room temperature. The crystalline slurry is suction filtered and washed with a mixture of ether and isopropanol (weight ratio 1:1). The product is practically colorless, and melts at 72° to 73° C. The yield is 80 to 90 percent of theory.

The water of crystallization may be easily removed under a water jet vacuum at from 70° to 110° C.

| Analysis: | C₉H₁₇NaO₆ (244) | | |
|---|---|---|---|
|  | C | H | Na |
| Calc.: | 44.3 | 7.0 | 9.4 |
| Found: | 43.8 | 7.0 | 9.0 |

EXAMPLE 1b o-(1-methoxyethoxy)-phenyl-(1'-butyn-3'-yl)-ether 244 parts by weight of the sodium salt of o-(1-methoxyethoxy)-phenol containing 3 molecules of water of crystallization, or 190 g of dehydrated salt is suspended in 300 parts by weight of dimethyl formamide. The mixture is heated to the boil while stirring and then 100 parts by weight of 1-butyn-3-yl chloride is dripped in. After approximately 1 hour the stoichiometric amount of sodium chloride has separated out. The mixture is allowed to cool and the sodium chloride is removed by suction filtration. The filtrate is concentrated, taken up in 1,000 parts of benzene and thoroughly washed twice, each time with 500 ml of 2N caustic soda solution. After drying over Na₂SO₄ has been effected the solvent is evaporated. Distillation is carried out after the addition of a spatula tip of succinic acid.

Yield: 182 parts by weight; b.p. (0.2 mm): 100° to 110° C.

| Analysis: | C₁₃H₁₆O₃ (220) | |
|---|---|---|
|  | C | H |
| Calc.: | 70.9 | 7.3 |
| Found: | 70.5 | 7.5 |

EXAMPLE 2 o-(1-methoxyethoxy)-phenyl isopropyl ether

The procedure of Example 1b is adopted except that 150 parts by weight of isopropyl bromide is used instead of 1-butyn-3-yl chloride.

B.p. (0.2 mm): 60° to 66° C.

EXAMPLE 3 o-(1-methoxyethoxy)-phenyl-(1'-buten-3'-yl)-ether

The procedure of Example 1b is adopted except that 110 parts by weight of 1-buten-3-yl chloride is used instead of 1-butyn-3-yl chloride.

B.p. (0.3 mm): 80° to 91° C.

| Analysis: | C₁₃H₁₈O₃ (222) | |
|---|---|---|
|  | C | H |
| Calc.: | 70.3 | 8.1 |
| Found: | 70.4 | 8.3 |

EXAMPLE 4 o-(1-ethoxyethoxy)-phenyl-(1'-butyn-3'-yl)-ether 440 parts by weight of pyrocatechol is dissolved in 1,500 parts of tetrahydrofuran. 1 ml of concentrated hydrochloric acid is added and 303 parts by weight of vinyl ethyl ether is then dripped in. The mixture is then kept for 1 hour at 65° C. and subsequently allowed to cool. There is added 720 parts by weight of a 30 wt percent technical grade NaOCH₃/CH₃OH solution. 400 parts by weight of 1-butyn-3-yl chloride is then added and the mixture heated under reflux until it shows a neutral reaction. Precipitated sodium chloride is filtered off and the filtrate concentrated. The oil remaining is dissolved in 3,000 parts of benzene and washed 5 times, each time with 1,000 parts of 2N aqueous NaOH. Drying is subsequently carried out over Na₂SO₄. The solvent is evaporated off and distillation effected after the addition of 2 parts by weight of succinic acid.

Boiling point (0.2 mm): 100° to 111° C.

| Analysis: | C₁₄H₁₈O₃ (234) | |
|---|---|---|
|  | C | H |
| calc.: | 71.8 | 7.7 |
| found: | 70.6 | 8.0 |

EXAMPLE 5 o-(1-methoxyethoxy)-phenyl benzyl ether

The procedure of Example 4 is adopted except that 133 parts by weight of benzyl chloride is used instead of 1-butyn-3-yl chloride. The mixture is heated under reflux until it shows a neutral reaction.

Yield: 175 parts by weight; boiling point (0.2 mm): 130° to 150° C.

The pyrocatechol ethers of the general formula II are obtained in a simple manner and excellent yields when pyrocatechol is reacted with preferably the amount required for etherification of one hydroxyl group of pyrocatechol, or up to about a 50 percent excess or deficiency of this amount, of a vinyl ether of the formula:

where $R^4$ is vinyl or vinyl bearing lower alkyl (up to $C_3$) as a substituent and $R^3$ has the above meanings, if necessary with the addition of catalytically active substances such as compounds having an acid reaction, for instance mineral acids, acid salts, organic acids, α-halo ethers, and organic and inorganic acid chlorides, and ion exchangers and Lewis acids, e.g. $AlCl_3$, $FeCl_3$, $BF_3$, etc. Etherification is carried out at from $-5°$ to $+120°$ C., preferably 40° to 50° C. and with or without the addition of solvents or diluents (e.g. 5 to 80 wt percent), e.g. ethers (diethyl ether, tetrahydrofuran, dioxane), hydrocarbons (e.g. n-hexane, benzene, toluene, xylene) and halohydrocarbons ($CH_2Cl_2$, $CHCl_3$, $CCl_4$), which are inert to the reactants.

When pyrocatechol is reacted with vinylmethyl ether, the reaction may be represented by the following equation:

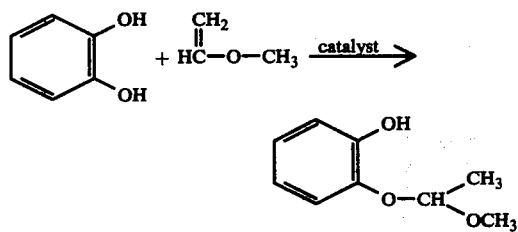

The catalysts used are preferably those mentioned above.

The pyrocatechol ethers may also be prepared by reaction of preferably equimolar amounts or with up to approx. 50 percent more or less the molar amount of α-halo ethers of the formula

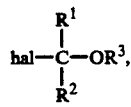

where hal denotes Cl, Br and I, $R^1$, $R^2$ and $R^3$ have the meanings set forth above in formula (I), with salts of pyrocatechol or with pyrocatechol in the presence of preferably equimolar amounts of organic or inorganic bases (e.g. alcoholates, alkali metal and alkaline earth metal hydroxides, and suitable amines) or of substances having an alkaline action, for instance alkali metal and alkaline earth metal carbonates.

The reaction is illustrated by the following equation:

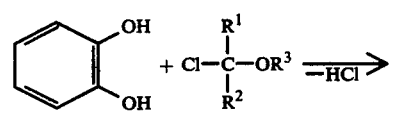

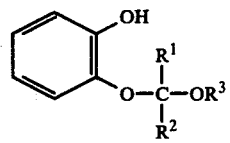

The radicals $R^1$, $R^2$ and $R^3$ have the meanings given above. The reactants are preferably diluted, e.g. with 5 to 80 wt percent of ether (diethyl ether, tetrahydrofuran) or hydrocarbons (n-hexane, benzene, toluene, xylene).

The vinyl and α-halo ethers used for the reaction are known from the literature and are simple to manufacture on an industrial scale (cf., for example, W. Reppe et al, Ann. Chem., 601, 98, 1956).

Depending on the excess amounts of vinyl and α-halo ethers used in the above processes, corresponding amounts of bis-ethers of the formula

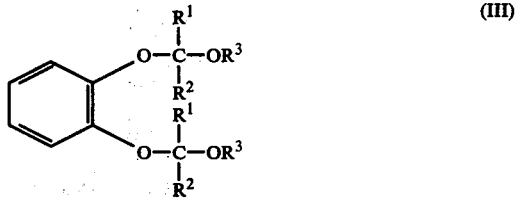

$R^1$, $R^2$ and $R^3$ having the above meanings, are formed.

The bis-ethers may be produced in quantitative yield preferably by reaction of pyrocatechol with at least twice the molar amount of a vinyl ether.

The catalysts and reaction conditions are similar to those employed in the preparation of compounds of the formula II.

Compounds of the formula II may also be prepared by reacting a bis-ether of the formula III with pyrocatechol in accordance with the following equation:

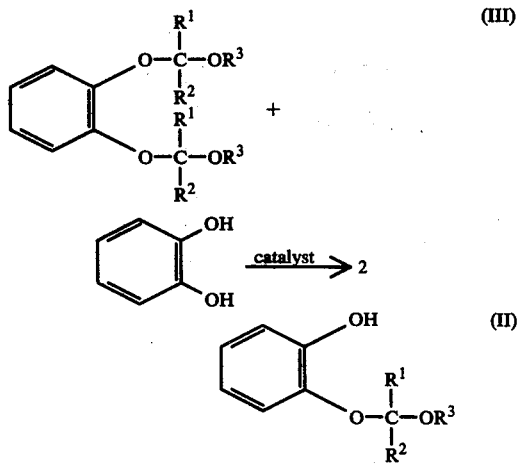

The radicals $R^1$, $R^2$ and $R^3$, the catalysts and the reaction conditions are the same as in the preparation of compounds of the formula II from vinyl ethers.

The pyrocatechol derivatives of formulae II and III are obtained as colorless oils which, after having been stabilized with organic or inorganic bases, may be distilled in vacuo without decomposition occurring. The compound are listed below:

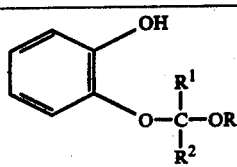
(II)

| R¹ | R² | R³ | b.p. °C; $n_D^{25}$ |
|---|---|---|---|
| H | H | CH₃ | b.p. (0.4 mm): 89 to 93 |
| H | H | C₂H₅ | b.p. (0.1 mm): 90 to 100 |
| H | CH₃ | CH₃ | b.p. (0.5 mm): 85 to 90 |
| H | CH₃ | C₂H₅ | b.p. (1 mm): 78 to 81 |
| H | CH₃ | n-C₃H₇ | b.p. (1 mm): 96 to 98 |
| H | CH₃ | i-C₃H₇ | b.p. (1 mm): 89 to 94 |
| H | CH₃ | i-C₄H₉ | b.p. (0.2 mm): 94 to 98 |
| H | CH₃ | 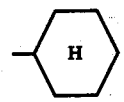 | b.p. (0.2 mm): 128 to 135 |
| H | CH₃ | 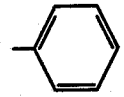 | b.p. (4 mm): 132 to 136 |
| H | CH₃ | COCH₃ | $n_D^{25}$: 1.5075 |
| H | CH₃ | COC₂H₅ | $n_D^{25}$: 1.4905 |
| H | CH₃ | —CH₂—CH=CH₂ | |
| H | CH₃ | —CH₂—C≡CH | |
| H | CH₃ | —CH(CH₃)—C≡CH | |
| H | CH₃ | —CH₂—CH₂—OCH₃ | |
| H | CH₃ | —CH₂—CH₂—OC₂H₅ | |
| H | CH₂Cl | —CH₃ | $n_D^{25}$: 1.5135 |
| H | CH₂Cl | —C₂H₅ | $n_D^{25}$: 1.5146 |
| H | CH₂Cl | —CH₂—CH₂Cl | $n_D^{25}$: 1.4975 |
| H | CH₂Cl | —COCH₃ | $n_D^{25}$: 1.5012 |
| H | CH₂Br | CH₃ | $n_D^{25}$: 1.5340 |
| H | CH₂J | CH₃ | |
| H | C₂H₅ | CH₃ | b.p. (1.5 mm): 105 to 113 |
| H | C₂H₅ | C₂H₅ | b.p. (0.5 mm): 100 to 103 |
| H | C₂H₅ | CH₂—C≡CH | |
| H | CH₂—CH₂Cl | CH₃ | $n_D^{25}$: 1.5023 |
| H | CH₂—CHCl—CH₃ | CH₃ | |
| H | CH₂—CHBr—CH₃ | CH₃ | |
| H | CH₂—CHCl—C₂H₅ | CH₃ | |
| H | n-C₃H₇ | CH₃ | |
| H | i-C₃H₇ | CH₃ | |
| H | CH=CH₂ | CH₃ | |
| H | C≡CH | CH₃ | |
| H | CH₂—C≡CH | CH₃ | |
| H | 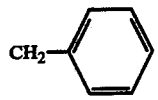 | CH₃ | |
| CH₃ | CH₃ | CH₃ | |
| CH₃ | CH₃ | C₂H₅ | |
| CH₃ | CH₂Cl | CH₃ | $n_D^{25}$: 1.5024 |
| CH₃ | CH₂Cl | C₂H₅ | |
| CH₃ | CH₂Br | CH₃ | |
| CH₃ | CH₂Br | C₂H₅ | |
| CH₃ | C₂H₅ | CH₃ | |
| CH₃ | n-C₃H₇ | CH₃ | |
| C₂H₅ | C₂H₅ | CH₃ | |
|  | | CH₃ | |
|  | | | |
| 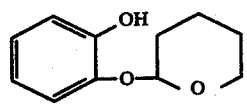 | | | b.p. (0.5 mm): 115 to 118 |

-continued $$\begin{array}{c} \text{(II)} \\ \underset{\substack{|\\R^2}}{\overset{\substack{R^1\\|}}{\text{O}-\text{C}-\text{OR}^3}} \\ \underset{\substack{|\\R^2}}{\overset{\substack{R^1\\|}}{\text{O}-\text{C}-\text{OR}^3}} \end{array}$$

| $R^1$ | $R^2$ | $R^3$ | b.p. °C |
|---|---|---|---|
| H | H | $CH_3$ | b.p. (0.4 mm): 105 to 109 |
| H | $CH_3$ | $CH_3$ | b.p. (0.5 mm): 99 to 105 |
| H | $CH_3$ | $C_2H_5$ | b.p. (0.3 mm): 97 to 102 |
| H | $CH_3$ | i-$C_4H_9$ | b.p. (0.3 mm): 124 to 128 |

EXAMPLE 6a o-(1-methoxyethoxy)-phenol 110 parts by weight of pyrocatechol is suspended in 100 parts by weight of toluene. At +5° C., 64 parts by weight of vinylmethyl ether at −40° C. is introduced all at once into the suspension and a drop of concentrated hydrochloric acid is then added. The mixture is heated, with stirring, to about +20° C., whereupon the reaction is initiated and the temperature in the flask rises to about 65° C. If necessary, ice water may be used for external cooling. The mixture is kept for 30 minutes at 65° C. and 5 parts by weight of 2N NaOH is then added. After the mixture has been cooled and dried with $Na_2SO_4$ the solvent is evaporated in a rotary evaporator and distillation carried out in vacuo.

Yield: 155 parts by weight; b.p. (0.5 mm): 85° to 90° C.

| Analysis: | $C_9H_{12}O_3$ (168) | |
|---|---|---|
| | C | H |
| calc.: | 64.1 | 7.2 |
| found: | 64.4 | 7.0 |

EXAMPLE 6b pyrocatechol-bis-[(1-methoxy)-ethyl ether]

Adopting the same procedure as in Example 1a, with the exception that twice the amount (128 parts by weight) of vinylmethyl ether is used, 122 parts by weight of a colorless oil is obtained.

Boiling point (0.5 mm): 99° to 105° C.

| Analysis: | $C_{12}H_{18}O_4$ (226) | |
|---|---|---|
| | C | H |
| calc.: | 63.7 | 8.0 |
| found: | 63.3 | 8.1 |

EXAMPLE 6c o-(1-methoxyethoxy)-phenol

At 40° C., 0.5 part of $SOCl_2$ is added to 113 parts by weight of pyrocatechol bis-[(1-methoxy)-ethyl ether] and 55 parts by weight of pyrocatechol and the mixture stirred for 30 minutes at this temperature. The mixture is cooled, 2 ml of 25 wt percent aqueous NaOH solution is added, the product is separated and dried over $Na_2SO_4$ and the solvent evaporated.

Yield: 168 parts; b.p. (0.5 mm): 85° to 90° C.

EXAMPLE 7a o-(1-ethoxyethoxy)-phenol 220 parts by weight of pyrocatechol is suspended in 200 parts by weight of toluene, 2 drops of concentrated hydrochloric acid are added and then, while stirring, 150 parts by weight of ethyl vinyl is dripped in. The internal temperature is prevented from rising above 65° C. by external cooling with ice water. Upon conclusion of the reaction all the pyrocatechol has dissolved. 5 parts by weight of 2N NaOH is added to the mixture which is then allowed to cool. The product is dried over $Na_2SO_4$ and, after removal of the solvent, distilled in vacuo.

Yield: almost quantitative; b.p. (1 mm): 78° to 81° C. $n_D^{25}$: 1.5032

| Analysis: | $C_{10}H_{14}O_3$ (182) | |
|---|---|---|
| | C | H |
| calc.: | 66.0 | 7.7 |
| found: | 66.3 | 7.9 |

EXAMPLE 7b pyrocatechol bis-[(1-ethoxy)-ethyl ether]

If 300 parts by weight of ethyl vinyl ether is used instead of 150 parts, 248 parts by weight of a colorless oil is obtained.

Boiling point (0.3 mm): 97° to 102° C.

| Analysis: | $C_{14}H_{22}O_4$ (254) | |
|---|---|---|
| | C | H |
| calc.: | 66.2 | 8.6 |
| found: | 66.4 | 8.7 |

EXAMPLE 7c o-(1-ethoxyethoxy)-phenol 127 parts by weight of pyrocatechol bis-[(1-ethoxy)-ethyl ether] and 55 parts by weight of pyrocatechol are reacted and the mixture worked up as in Example 11c.

Yield: 179 parts; b.p. (1 mm): 79° to 80° C.

EXAMPLE 8 o-(methoxymethoxy)-phenol 110 parts by weight of pyrocatechol is dissolved in 400 parts by weight of benzene. At room temperature there are simultaneously dripped into this solution 101 parts by weight of triethylamine and 81 parts by weight of chloromethyl methyl ether in such a manner that the reaction medium has a weakly alkaline reaction. Subsequently the mixture is heated for an hour under reflux and then allowed to cool. The hydrochloride is removed by suction filtration and the product is washed, dried over Na$_2$SO$_4$, concentrated and distilled in vacuo.

Yield: 120 parts by weight; b.p. (0.4 mm): 89° C; n$_D^{25}$: 1.5150

|  | C$_8$H$_{10}$O$_3$ (154) | |
|---|---|---|
| Analysis: | C | H |
| calc.: | 62.3 | 6.5 |
| found: | 62.0 | 6.5 |

The pyrocatechol bis-ethers of the general formula II are important intermediates for pharmaceutical products and products for use in veterinary medicine and for production of active ingredients for plant protection agents.

The pyrocatechol bis-ethers of the general formula I can be converted to monoethers of the general formula IV

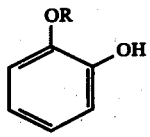

where R has the meaning set forth for I, in a simple manner and in excellent yield by cleaving the bis-ether I in an acid medium, e.g., by the action of aqueous acid or by an exchange reaction with lower (C$_1$ to C$_5$) alcohols or phenols with acid catalysis.

The reaction is illustrated for example by the following equation:

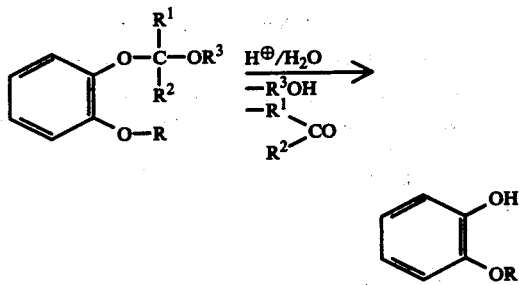

For instance, the starting materials are stirred, preferably at a temperature of from 40° to 100° C., in very dilute, e.g. 0.001% (by weight) aqueous mineral acid, e.g. H$_2$SO$_4$, HCl, HNO$_3$, H$_3$PO$_4$, until cleavage is over. If necessary, water-miscible solvents (e.g. alcohols, ketones and ethers) for increasing the solubility of the starting compounds may be added to the mixture in amounts of from 0.1 to 90% (by weight).

The pyrocatechol monoethers prepared in this manner and having the following formula:

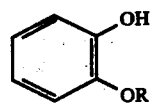

are given below:

| R | b.p.; m.p.; n$_D^{25}$ |
|---|---|
| CH$_3$ | b.p. (25 mm):105° C |
| C$_2$H$_5$ | b.p. (20 mm): 100° C |
| n-C$_3$H$_7$ | b.p. (14 mm): 110° to 114°C |
| i-C$_3$H$_7$ | b.p. (0.2 mm): 66° C |
| —CH$_2$—CH=CH$_2$ | b.p. (12 mm): 110° C |
| —CH(CH$_3$)—CH=CH$_2$ | b.p. (0.4 mm): 68° to 84° C |
| —CH$_2$—CH=CH—CH$_3$ | |
| —CH$_2$—CH=CCl—CH$_3$ | n$_D^{25}$: 1,4875 |
| —CH$_2$—C(Cl)=C(H)(Cl) | n$_D^{25}$: 1,5295 |
| —CH$_2$—C(CH$_3$)=CCl$_2$ | n$_D^{25}$: 1,5027 |
| —CH$_2$—C≡CH | m.p.: 49° to 50° C |
| —CH$_2$—C≡C—CH$_3$ | m.p.: 44° to 47° C |
| —CH$_2$—C≡C—C$_2$H$_5$ | n$_D^{25}$: 1,5360 |
| —CH(CH$_3$)—C≡CH | m.p.: 52° to 53° C |

The preparation of the monoether is illustrated by the following example.

EXAMPLE 9 o-(1-butyn-3-yloxy)-phenol 220 parts by weight of o-(1-methoxyethoxy)-phenyl-(1'-butyn-3'-yl)-ether is slowly dripped into a well-stirred mixture, boiling under reflux, of 2,000 parts by weight of water, 500 parts by weight of ethanol and 2 parts by weight of concentrated sulfuric acid. The whole is then stirred for a further 2 hours under reflux and subsequently allowed to cool. Extraction is then carried out 3 times, each time with 150 parts by weight of chloroform. After drying over Na$_2$SO$_4$ the solvent is evaporated off, and the oil which remains crystallizes after having been allowed to stand for a short period of time. Thin-layer chromatography shows the substance to be uniform.

Yield: 126 parts by weight; m.p.: 52° to 53° C.

The prior art active ingredients for use in plant protection agents are prepared by known methods. The monoethers of the general formula V can be further processed by known methods by treating IV with methyl isocyanate to form N-methylphenyl carbamates of the general formula V.

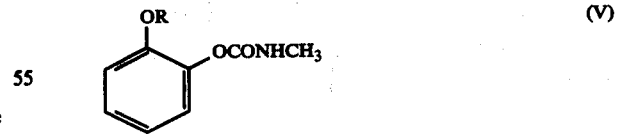

For example U.S. Pat. No. 3,111,539 discloses that the reaction of O-isopropoxy phenol can be treated with methyl isocyanate to yield the well-known insecticidal active ingredient O-isopropoxyphenyl-N-methylcarbamate. Similarly, carbamates of the formula V where R is alkynyl are known from U.S. Pat. No. 3,910,991, U.S. Pat. No. 3,931,408, and U.S. application Ser. No. 35,282. The latter discloses the preparation of O-(2-butyn-1'-yl-3'-oxyphenyl)-N-methylcarbamate (Example 1) and O-(2-butyn-2'-yl-1'-oxyphenyl)-N-methylcarbamate (Example 2) and their utility as insecticides. Also, it is known to prepare O-propargoxyphenol-N-methylcarbamate from O-propargoxyphenol and methyl isocyanate (U.S. Pat. No. 3,202,573). The carbamate is a known pesticide.

We claim:

1. A pyrocatechol bis-ether of the formula

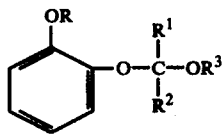

R denotes alkyl of from 1 to 4 carbon atoms which may be substituted with halogen; alkenyl having up to 4 carbon atoms which may be substituted with halogen; alkynyl having up to 5 carbon atoms which may be substituted with halogen; or benzyl;

$R^1$ denotes hydrogen or alkyl of from 1 to 4 carbon atoms;

$R^2$ denotes benzyl or alkyl of from 1 to 3 carbon atoms which may be substituted with halogen, methoxy or ethoxy;

$R^3$ denotes alkyl of from 1 to 4 carbon atoms; cycloalkyl of from 3 to 7 carbon atoms; $\beta$-chlorethyl; methoxyethyl; ethoxyethyl; alkenyl of from 2 to 4 carbon atoms; alkynyl of from 2 to 4 carbon atoms.

2. A pyrocatechol bis-ether as set forth in claim 1, wherein the pyrocatechol bis-ether is o-(1-methoxyethoxy)-phenyl isopropyl ether.

3. A pyrocatechol bis-ether as set forth in claim 1, wherein the pyrocatechol bis-ether is o-(1-methoxyethoxy)-phenyl-(1'-butyn-3'-yl)-ether.

4. A pyrocatechol bis-ether as set forth in claim 1, wherein the pyrocatechol bis-ether is o-(1-ethoxyethoxy)-phenyl-(1'-butyn-3'-yl)-ether.

* * * * *